United States Patent
Tanaka et al.

(10) Patent No.: US 8,222,433 B2
(45) Date of Patent: Jul. 17, 2012

(54) AXIALLY ASYMMETRIC PHOSPHORUS COMPOUND AND PRODUCTION METHOD THEREOF

(75) Inventors: Ken Tanaka, Tokyo (JP); Tohru Yokozawa, Kanagawa (JP); Tomohiko Hakamata, Kanagawa (JP)

(73) Assignees: National University Corporation Tokyo University of Agriculture and Technology, Tokyo (JP); Takasago International Corporation, Tokyo (JP)

( * ) Notice: Subject to any disclaimer, the term of this patent is extended or adjusted under 35 U.S.C. 154(b) by 0 days.

(21) Appl. No.: 13/041,621

(22) Filed: Mar. 7, 2011

(65) Prior Publication Data
US 2011/0218345 A1 Sep. 8, 2011

(30) Foreign Application Priority Data
Mar. 8, 2010 (JP) ................. 2010-050267

(51) Int. Cl.
*C07F 9/53* (2006.01)
(52) U.S. Cl. .................................... 549/220
(58) Field of Classification Search .......... 549/458, 549/220
See application file for complete search history.

(56) References Cited

U.S. PATENT DOCUMENTS
2009/0227805 A1* 9/2009 Tanaka et al. ............ 549/220

FOREIGN PATENT DOCUMENTS
EP 2 098 531 9/2009

OTHER PUBLICATIONS

Extended European Search Report issued Jun. 24, 2011 in European Application No. 11154933.3.
F. Mori et al., "Asymmetric Synthesis of Axially Chiral Biaryl Diphosphine Ligands by Rhodium-Catalyzed Enantioselective Intramolecular Double [2+2+2] Cycloaddition", Organic Letters, vol. 13, No. 3, pp. 362-365, 2011.
S. Doherty et al., "Rhodium-Catalyzed Double [2+2+2] Cycloaddition of 1,4-Bis(diphenylphosphinoyl)buta-1,3-diyne with Tethered Diynes: A Modular, Highly Versatile Single-Pot Synthesis of NU-BIPHEP Biaryl Diphosphines", Organic Letters, vol. 9, No. 23, pp. 4925-4928, Oct. 16, 2007.

* cited by examiner

Primary Examiner — Golam M M Shameem
Assistant Examiner — Karen Cheng
(74) Attorney, Agent, or Firm — Wenderoth, Lind & Ponack, L.L.P.

(57) ABSTRACT

An optically active compound represented by the following formula (5):

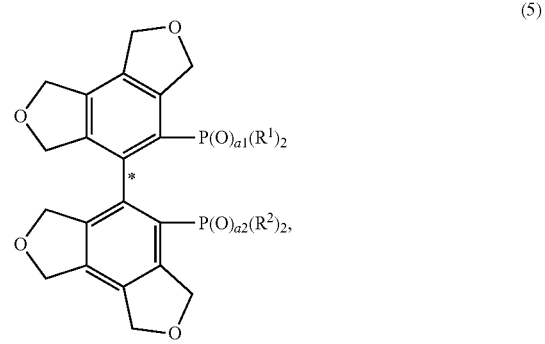

(5)

wherein, in the formula (5), $R^1$ and $R^2$ may be the same or different are an alkyl group optionally having a substituent group selected from the group consisting of an alkoxy group and a halogen atom, a cycloalkyl group optionally having a substituent group selected from the group consisting of an alkoxy group and a halogen atom, an aryl group optionally having a substituent group selected from the group consisting of an alkyl group, an alkoxy group and a halogen atom, an alkoxy group optionally having a substituent group selected from the group consisting of a halogen atom and an aryl group or an aryloxy group optionally having a substituent group selected from the group consisting of an alkyl group, an alkoxy group and a halogen atom; a1 and a2 independently are 0 or 1; and * is axial asymmetry.

6 Claims, No Drawings

AXIALLY ASYMMETRIC PHOSPHORUS COMPOUND AND PRODUCTION METHOD THEREOF

This application claims the benefit of Japanese Application No. 2010-050267, filed Mar. 8, 2010.

The present invention relates to an axially asymmetric phosphorus compound useful as a ligand of a metal catalyst and a production method thereof.

BACKGROUND ART

Until now, many reports have been published on transition metal complexes usable as a catalyst for an asymmetric reaction such as asymmetric hydrogenation reaction, asymmetric isomerization reaction, and asymmetric hydrosilylation reaction. In particular, complexes containing a transition metal such as ruthenium, rhodium, iridium, palladium, or the like and an optically active phosphine compound coordinated to the metal have widely been known as a high performance catalyst for an asymmetric synthesis reaction. Among such optically active phosphine compounds, an optically active biaryl phosphine compound with axial asymmetry is useful as an optically active ligand of an asymmetric reaction catalyst. Recently, as a new technique for synthesizing an optically active biaryl compound, a technique involving an enantioselective [2+2+2] cycloaddition reaction using alkynes has also been developed (US 2009/0227805 A1, Organic Letters, 2006, Vol. 8, 3489-3492, Organic Letters, 2008, Vol. 10, 2849-2852).

DISCLOSURE OF THE INVENTION

Problems to be Solved

As described above, although the synthesis of a biaryl compound having an axially asymmetric structure by way of an enantio-selective [2+2+2] cycloaddition reaction has been known, process for synthesizing a compound with a phosphorus atom site introduced into the 2,2' site of the biaryl skeleton thereof is hitherto known. However, it was reported about only a bicyclobiaryl compound.

In this context, if it is possible to synthesize an axially asymmetric biaryl phosphorus compound in high optical purity from a substrate relatively easy to obtain through a reduced number of steps, an axially asymmetric optically active substance can easily be obtained without the step of optical resolution, which is almost indispensable step in a conventional method. The objective of the present invention is to provide such a production method and an axially asymmetric biaryl phosphorus compound to be produced in such a manner.

Means for Solving the Problems

To solve the problems, the inventors have found that an axially asymmetric biaryl phosphorus compound having high optical purity can be produced in one step by an enantioselective [2+2+2] cycloaddition reaction of a compound having plural triple bonds in the presence of a catalyst containing rhodium and an optically active bisphosphine, and have completed the present invention.

The present invention includes:

[1]. a method for producing an optically active compound represented by the following general formula (1) which comprises an intramolecular cycloaddition reaction of a compound represented by the following general formula (2) with the use of a catalyst containing rhodium metal and an optically active bisphosphine:

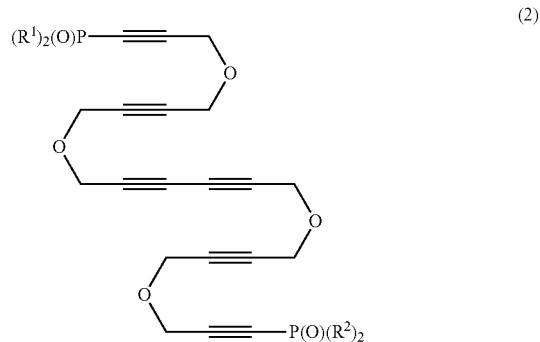

(where, in the formula (2), $R^1$ and $R^2$ may be the same or different are an alkyl group optionally having a substituent group, a cycloalkyl group optionally having a substituent group, an aryl group optionally having a substituent group, an alkoxy group optionally having a substituent group or an aryloxy group optionally having a substituent group;

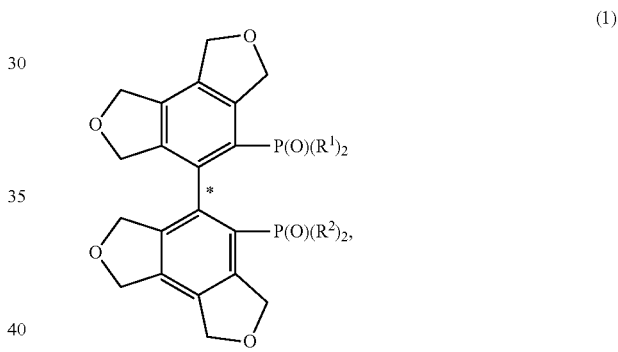

(where, in the formula (1), $R^1$ and $R^2$ may be the same or different and independently are an alkyl group optionally having a substituent group, a cycloalkyl group optionally having a substituent group, an aryl group optionally having a substituent group, an alkoxy group optionally having a substituent group or an aryloxy group optionally having a substituent group; and * is axial asymmetry;

[2]. the method according to the above-mentioned [1], wherein the catalyst containing rhodium metal and an optically active bisphosphine is a compound represented by the following general formula (3):

$$[Rh(L)_m(Y)_n]X \qquad (3)$$

(where, in the formula (3), L is an optically active bisphosphine represented by the following formula (4);

Y is a nonconjugated diene compound; X is a counter anion; m is an integer 1 or 2; n is an integer 0 or 1; when m is 1, n is 0 or n is 1; and when m is 2, n is 0):

$$R^3R^4P\text{-}Q\text{-}PR^5R^6 \qquad (4)$$

(where, in the formula (4), $R^3$, $R^4$, $R^5$, and $R^6$ independently are an aryl group optionally having a substituent group, a cycloalkyl group optionally having a substituent group or an alkyl group optionally having a substituent group; $R^3$ in combination with $R^4$ and/or $R^5$ in combination with $R^6$ may form a ring; and Q is a divalent arylene group optionally having a substituent group or a ferrocenediyl group optionally having a substituent group);

[3]. the method according to the above-mentioned [2], wherein an olefinic ligand is eliminated with the use of hydrogen gas in preparing the catalyst containing rhodium metal and an optically active bisphosphine;

[4]. a compound represented by the following general formula (2):

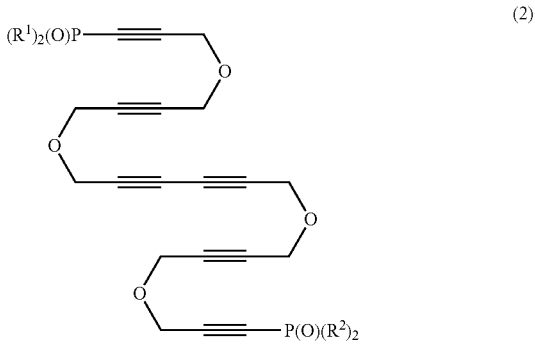

(2)

(where, in the formula (2), $R^1$ and $R^2$ may be the same or different are an alkyl group optionally having a substituent group, a cycloalkyl group optionally having a substituent group, an aryl group optionally having a substituent group, an alkoxy group optionally having a substituent group or an aryloxy group optionally having a substituent group; and

[5]. an optically active compound which is obtained by the method according to the above-mentioned [1], [2] or [3] represented by the following general formula (5):

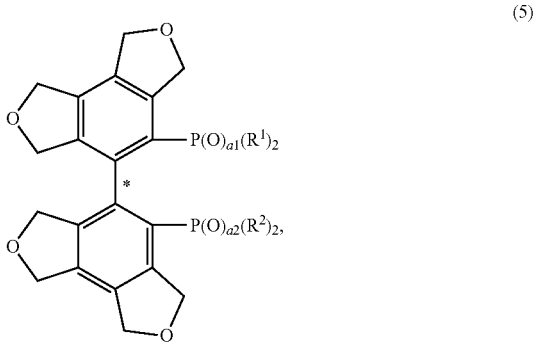

(5)

(where, in the formula (5), $R^1$ and $R^2$ may be the same or different are an alkyl group optionally having a substituent group, a cycloalkyl group optionally having a substituent group, an aryl group optionally having a substituent group, an alkoxy group optionally having a substituent group or an aryloxy group optionally having a substituent group; a1 and a2 independently are 0 or 1; and * is axial asymmetry).

Effects of the Invention

According to the process of the invention, since it is possible to enantio-selectively produce an optically active biaryl phosphorus compound in one step by reacting a compound having a plurality of triple bonds and a phosphorus compound in the presence of a catalyst containing rhodium metal and an optically active bisphosphine, an axially asymmetric substance can be obtained without the step of optical resolution. Furthermore, an optically active biaryl phosphorus compound within the scope of the invention can easily be produced with the use of a substrate relatively easy to obtain and is useful as a ligand of a metal catalyst.

MODES FOR CARRYING OUT THE INVENTION

Hereinafter, the invention will be described in more detail.

A phosphorus compound of the invention is a phosphorus compound represented by the above-mentioned general formula (1), (2), and (5), and can be produced by the production method of the invention, which will be described in detail below. In the general formulas (1), (2), and (5), and $R^1$ and $R^2$ are an alkyl group optionally having a substituent group, a cycloalkyl group optionally having a substituent group, an aryl group optionally having a substituent group, an alkoxy group optionally having a substituent group or an aryloxy group optionally having a substituent group.

Herein, the alkyl group represented by $R^1$ and $R^2$ may be, for example, a linear or branched alkyl group having 1 to 15 carbon atoms, preferably 1 to 10 carbon atoms, more preferably 1 to 6 carbon atoms. Specific examples include, for example, a methyl, ethyl, n-propyl, isopropyl, n-butyl, s-butyl, isobutyl, t-butyl, pentyl, and hexyl group. These alkyl groups may have a substituent group, and the examples of the substituent group include, for example, an alkoxy group and a halogen atom.

The cycloalkyl group represented by $R^1$ or $R^2$ may be a cycloalkyl group having 3 to 12 carbon atoms, and specific examples include a cyclopropyl, cyclobutyl, cyclopentyl, cyclohexyl, cycloheptyl, cyclooctyl, and adamantyl group. These cycloalkyl groups may have a substituent group, and the examples of the substituent group include, for example, an alkoxy group and a halogen atom.

The aryl group represented by $R^1$ or $R^2$ may be an aryl group having 6 to 18 carbon atoms, and specific examples include a phenyl, naphthyl, anthryl, phenanthryl, and biphenyl group. These aryl groups may have a substituent group and examples of the substituent group include linear or branched alkyl groups having 1 to 6 carbon atoms such as methyl and t-butyl; linear or branched alkoxy groups having 1 to 6 carbon atoms such as methoxy and t-butoxy; and halogen atoms such as chlorine, bromine, and fluorine; and a plurality of these substituent groups may be introduced into the aryl groups. Specific examples of these aryl groups having a substituent group include, for example, a p-tolyl, m-tolyl, o-tolyl, 3,5-xylyl, 3,5-di-t-butylphenyl, p-t-butylphenyl, p-methoxyphenyl, 3,5-di-t-butyl-4-methoxyphenyl, p-chlorophenyl, m-chlorophenyl, p-fluorophenyl, and m-fluorophenyl group.

The alkoxy group represented by $R^1$ or $R^2$ may be, a linear or branched alkoxy group, for example, having 1 to 15 carbon atoms, preferably 1 to 10 carbon atoms, and more preferably 1 to 6 carbon atoms. Specific examples include, for example, a methoxy, ethoxy, n-propoxy, isopropoxy, n-butoxy, s-butoxy, isobutoxy, t-butoxy, pentyloxy, and hexyloxy group. These alkoxy groups may have a substituent group, and the examples of the substituent group include, for example, a halogen atom and an aryl group.

The aryloxy group represented by $R^1$ or $R^2$ may be an aryloxy group having 6 to 18 carbon atoms, and specific examples are phenyloxy, naphthyloxy, anthryloxy, phenanthryloxy, and biphenyloxy. These aryloxy groups may have a substituent group and examples of the substituent group include linear or branched alkyl groups having 1 to 6 carbon atoms such as methyl and t-butyl; linear or branched alkoxy groups having 1 to 6 carbon atoms such as methoxy and t-butoxy; and halogen atoms such as chlorine, bromine, and fluorine, and a plurality of these substituent groups may be introduced into the aryl group.

Next, a method for producing an axially asymmetric optically active phosphorus compound, which can be used for producing the phosphorus compound of the invention (referred to simply as the production method of the invention in some cases), will be described.

As described in the following scheme 1, the production method of an axially asymmetric optically active phosphorus compound of the invention causes reaction in the presence of a catalyst containing rhodium metal and an optically active bisphosphine compound, and more particularly causes enantio-selective [2+2+2] cycloaddition.

SCHEME 1

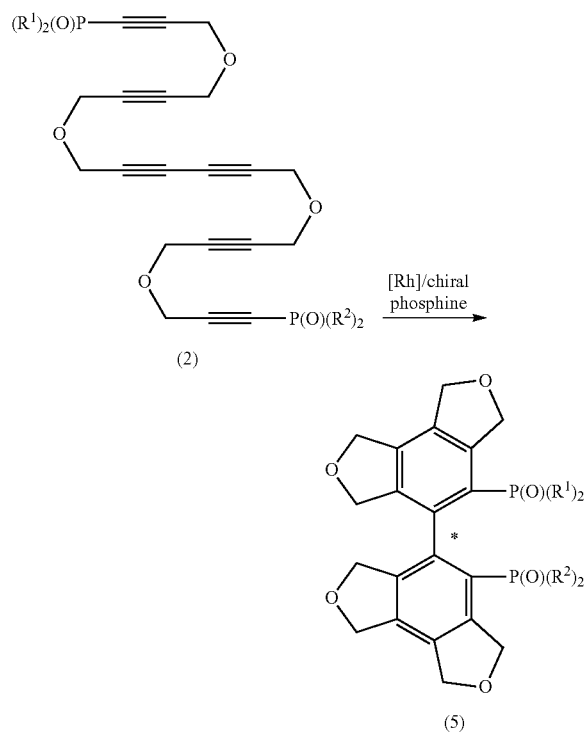

Definitions of the reference characters and examples of the groups represented by these reference characters described also in the schemes are the same as those described above.

The catalyst containing rhodium metal and an optically active bisphosphine compound used in the production method of the invention will be described.

As the rhodium source for the rhodium metal used as one component of the catalyst of the invention, rhodium compounds may be used, and preferable rhodium compounds may be complexes of rhodium(I) coordinated with an olefinic ligand. Specific examples of rhodium(I) complexes are [Rh(COD)$_2$]X, [Rh(NBD)$_2$]X, [Rh(ethylene)$_2$Cl]$_2$, [Rh(COE)$_2$Cl]$_2$. [Rh(COD)Cl]$_2$, and [Rh(NBD)Cl]$_2$. In the above-mentioned chemical formulas of the complexes, X is a counter anion such as Cl, Br, I, BF$_4$, OTf, ClO$_4$, SbF$_6$, BPh$_4$, and B(3,5-(CF$_3$)$_2$C$_6$H$_3$); COE is cyclooctene; COD is 1,5-cyclooctadiene; and NBD is norbornadiene.

Examples of the optically active bisphosphine compound that is the other catalytic component used for the invention are those represented by the following general formula (4):

$$R^3R^4P-Q-PR^5R^6 \qquad (4)$$

(where, in the formula (4), $R^3$, $R^4$, $R^5$, and $R^6$ independently are an aryl group optionally having a substituent group; or $R^3$ in combination with $R^4$ and/or $R^5$ in combination with $R^6$ may form a ring; and Q is a divalent arylene group optionally having a substituent group).

In the above formula, the aryl group denoted by $R^3$, $R^4$, $R^5$, or $R^6$ optionally having a substituent group may be an aryl group having 6 to 14 carbon atoms, and specific examples are phenyl, naphthyl, anthryl, phenanthryl, and biphenyl. These aryl groups may have a substituent group, and the substituent group may be an alkyl group, alkoxy group and halogen atom.

The alkyl group as a substituent group of the aryl group may include, for example, linear or branched alkyl groups having 1 to 15 carbon atoms, preferably 1 to 10 carbon atoms, and more preferably 1 to 6 carbon atoms, and specific examples are methyl, ethyl, n-propyl, isopropyl, n-butyl, s-butyl, isobutyl and t-butyl.

The alkoxy group as a substituent group of the aryl group may include, for example, linear or branched alkoxy groups having 1 to 6 carbon atoms, and specific examples are methoxy, ethoxy, n-propoxy, isopropoxy, n-butoxy, s-butoxy, isobutoxy and t-butoxy.

The halogen atom as a substituent group of the aryl group may include, for example, fluorine atom, chlorine atom and bromine atom.

Furthermore, the ring formed by combination of $R^3$ with $R^4$ and/or $R^5$ with $R^6$ may be a 4-, 5-, or 6-membered ring containing a phosphorus atom to which $R^3$, $R^4$, $R^5$, and $R^6$ are bound. Specific examples of the ring are a phosphetane, phospholane, phosphane, 2,4-dimethylphosphetane, 2,4-diethylphosphetane, 2,5-dimethylphospolane, 2,5-diethylphospholane, 2,6-dimethylphosphane, and 2,6-diethylphosphane ring. These rings may be optically active substances.

The divalent arylene group denoted by Q optionally having a substituent group may be a phenylene, biphenyldiyl, and binaphthalenediyl group. The phenylene group includes, for example, an o- or m-phenylene group, and may have a substituent group selected from an alkyl group such as a methyl, ethyl, n-propyl, isopropyl, n-butyl, s-butyl, isobutyl, and t-butyl group; an alkoxy group such as a methoxy, ethoxy, n-propoxy, isopropoxy, n-butoxy, s-butoxy, isobutoxy, and t-butoxy group; a hydroxyl group; an amino group; and a substituted amino group. The biphenyldiyl group and the binaphthalenediyl group are preferably have a 1,1'-biaryl-2,2'-diyl type structure, and may have a substituent group selected from the above-mentioned alkyl group and alkoxy group; an alkylenedioxy group such as methylenedioxy, ethylenedioxy, and trimethylenedioxy; a hydroxyl group; an amino group; and a substituted amino group.

Specific examples of the optically active bisphosphine compound represented by the general formula (4) may be a conventionally known bisphosphine, and one example is a compound represented by the following general formula (6).

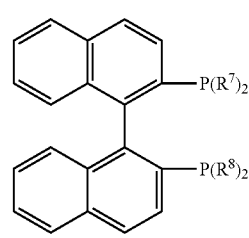

(In the formula, $R^7$ and $R^8$ independently are a phenyl group optionally having a substituent group selected from a halogen atom, an alkyl group, and an alkoxy group, or are a cyclopentyl group or a cyclohexyl group.)

In the above $R^7$ and $R^8$, the alkyl group as a substituent group of the phenyl may include, for example, linear or branched alkyl groups having 1 to 6 carbon atoms such as a methyl, ethyl, n-propyl, isopropyl, n-butyl, s-butyl, isobutyl and t-butyl group; the alkoxy group as a substituent group of the phenyl may include, for example, linear or branched alkoxy groups having 1 to 6 carbon atoms such as a methoxy, ethoxy, n-propoxy, isopropoxy, n-butoxy, s-butoxy, isobutoxy and t-butoxy group; and the halogen atom as a substituent group of the phenyl may include, for example, chlorine, bromine, and fluorine. A plurality of these substituent groups may be introduced into the phenyl group.

Specific examples of $R^7$ and $R^8$ are phenyl, p-tolyl, m-tolyl, o-tolyl, 3,5-xylyl, 3,5-di-t-butylphenyl, p-t-butylphenyl, p-methoxyphenyl, 3,5-di-t-butyl-4-methoxyphenyl, p-chlorophenyl, m-chlorophenyl, p-fluorophenyl, m-fluorophenyl, cyclopentyl, and cyclohexyl.

The binaphthyl ring that is the basic skeleton of the compound represented by the general formula (6) may have a substituent group, and the substituent group may include, for example, alkyl groups such as a methyl ethyl, n-propyl, isopropyl, n-butyl, s-butyl, isobutyl and t-butyl group; alkoxy groups such as a methoxy, ethoxy, n-propoxy, isopropoxy, n-butoxy, s-butoxy, isobutoxy and t-butoxy group; trialkylsilyl groups such as a trimethylsilyl, triisopropylsilyl, and t-butyldimethylsilyl group; and triarylsilyl groups such as a triphenylsilyl group.

Another specific example of the optically active bisphosphine compound represented by the general formula (4) may be a compound represented by the following general formula (7).

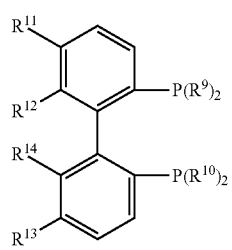

(7)

(In the formula, $R^9$ and $R^{10}$ independently are a phenyl group, a cyclopentyl or a cyclohexyl group optionally having a substituent group selected from a halogen atom, an alkyl group, and an alkoxy group. $R^{11}$ and $R^{13}$ may be the same or different are a hydrogen atom, an alkyl group or an alkoxy group; $R^{12}$ and $R^{14}$ may be the same or different are an alkyl group or an alkoxy group; $R^{11}$ and $R^{12}$ or/and $R^{13}$ and $R^{14}$ may form a methylene chain optionally having a substituent group or a (poly)methylenedioxy group optionally having a substituent group.)

In the above $R^9$ and $R^{10}$, the alkyl group as a substituent group of the phenyl may include, for example, linear or branched alkyl groups having 1 to 6 carbon atoms such as a methyl, ethyl, n-propyl, isopropyl, n-butyl, s-butyl, isobutyl and t-butyl group; the alkoxy group as a substituent group of the phenyl may include, for example, linear or branched alkoxy groups having 1 to 6 carbon atoms such as a methoxy, ethoxy, n-propoxy, isopropoxy, n-butoxy, s-butoxy, isobutoxy and t-butoxy group; and the halogen atom as a substituent group of the phenyl may include, for example, chlorine, bromine, and fluorine. A plurality of these substituent groups may be introduced into the phenyl group. Specific examples of $R^9$ and $R^{10}$ are phenyl, p-tolyl, m-tolyl, o-tolyl, 3,5-xylyl, 3,5-di-t-butylphenyl, p-t-butylphenyl, p-methoxyphenyl, 3,5-di-t-butyl-4-methoxyphenyl, p-chlorophenyl, m-chlorophenyl, p-fluorophenyl, m-fluorophenyl, cyclopentyl, and cyclohexyl.

The alkyl group denoted by $R^{11}$, $R^{12}$, $R^{13}$ and $R^{14}$ may include, for example, linear or branched alkyl groups having 1 to 6 carbon atoms such as a methyl, ethyl, n-propyl, isopropyl, n-butyl, s-butyl, isobutyl and t-butyl group; the alkoxy group may include for example, linear or branched alkoxy groups having 1 to 6 carbon atoms such as a methoxy, ethoxy, n-propoxy, isopropoxy, n-butoxy, s-butoxy, isobutoxy, t-butoxy group.

In the case where two of $R^{11}$ and $R^{12}$ and/or $R^{13}$ and $R^{14}$ form a methylene chain optionally having a substituent group, the methylene chain preferably includes, for example, methylene chains having 3 to 5 carbon atoms, and specific examples are trimethylene, tetramethylene, and pentamethylene. The substituent group in the methylene chain optionally having a substituent group may be an alkyl group or a halogen atom, and specific examples are the above-mentioned alkyl groups having 1 to 6 carbon atoms and a fluorine atom.

In the case where two of $R^{11}$ and $R^{12}$ and/or $R^{13}$ and $R^{14}$ form a (poly)methylenedioxy group optionally having a substituent group, specific examples of the (poly)methylenedioxy group are methylenedioxy, ethylenedioxy, and trimethylenedioxy. The substituent group in the (poly)methylenedioxy may be an alkyl group or a halogen atom, and specific examples are the above-mentioned alkyl groups having 1 to 6 carbon atoms and a fluorine atom.

Specific examples of the optically active bisphosphine compound represented by the general formula (6) or (7) are
2,2'-bis(diphenylphosphino)-1,1'-binaphthyl (BINAP),
2,2'-bis[di(p-tolyl)phosphino]-1,1'-binaphthyl (tol-BINAP),
2,2'-bis[di(m-tolyl)phosphino]-1,1'-binaphthyl,
2,2'-bis[di(3,5-xylyl)phosphino]-1,1'-binaphthyl (Xyl-BINAP),
2,2'-bis[di(p-t-butylphenyl)phosphino]-1,1'-binaphthyl,
2,2'-bis[di(p-methoxyphenyl)phosphino]-1,1'-binaphthyl,
2,2'-bis[di(3,5-di-t-butyl-4-methoxyphenyl)phosphino]-1,1'-binaphthyl,
2,2'-bis[di(cyclopentyl)phosphino]-1,1'-binaphthyl,
2,2'-bis[di(cyclohexyl)phosphino]-1,1'-binaphthyl,
2,2'-bis(diphenylphosphino)-5,5',6,6',7,7',8,8'-octahydro-1,1'-binaphthyl ($H_8$-BINAP),
2,2'-bis(di-p-tolylphosphino)-5,5',6,6',7,7',8,8'-octahydro-1,1'-binaphthyl,
2,2'-bis(di-m-tolylphosphino)-5,5',6,6',7,7',8,8'-octahydro-1,1'-binaphthyl,
2,2'-bis(di-3,5-xylylphosphino)-5,5',6,6',7,7',8,8'-octahydro-1,1'-binaphthyl,
2,2'-bis(di-p-t-butylphenylphosphino)-5,5',6,6',7,7',8,8'-octahydro-1,1'-binaphthyl,
2,2'-bis(di-p-methoxyphenylphosphino)-5,5',6,6',7,7',8,8'-octahydro-1,1'-binaphthyl,
2,2'-bis(di-p-chlorophenylphosphino)-5,5',6,6',7,7',8,8'-octahydro-1,1'-binaphthyl,
2,2'-bis(dicyclopentylphosphino)-5,5',6,6',7,7',8,8'-octahydro-1,1'-binaphthyl,
2,2'-bis(dicyclohexylphosphino)-5,5',6,6',7,7',8,8'-octahydro-1,1'-binaphthyl, ((4,4'-bi-1,3-benzodioxole)-5,5'-diyl)bis(diphenylphosphine)(Segphos),
((4,4'-bi-1,3-benzodioxole)-5,5'-diyl)bis(di(3,5-dimethylphenyl)phosphine),
((4,4'-bi-1,3-benzodioxole)-5,5'-diyl)bis(di(3,5-di-t-butyl-4-methoxyphenyl)phosphine),
((4,4'-bi-1,3-benzodioxole)-5,5'-diyl)bis(di(4-methoxyphenyl)phosphine),
((4,4'-bi-1,3-benzodioxole)-5,5'-diyl)bis(dicyclohexylphosphine),
((4,4'-bi-1,3-benzodioxole)-5,5'-diyl)bis(bis(3,5-di-t-butylphenyl)phosphine),
2,2'-bis(diphenylphosphino)-6,6'-dimethyl-1,1'-biphenyl,
2,2'-bis(di-p-tolylphosphino)-6,6'-dimethyl-1,1'-biphenyl,
2,2'-bis(di-o-tolylphosphino)-6,6'-dimethyl-1,1'-biphenyl,
2,2'-bis(di-m-fluorophenylphosphino)-6,6'-dimethyl-1,1'-biphenyl,
2,2'-bis(diphenylphosphino)-6,6'-dimethoxy-1,1'-biphenyl,
2,2'-bis(diphenylphosphino)-5,5',6,6'-tetramethoxy-1,1'-biphenyl,
2,2'-bis(di-p-tolylphosphino)-6,6'-dimethoxy-1,1'-biphenyl,
1,2-bis(2,5-dimethylphospholano)benzene,
1,2-bis(2,5-diethylphospholano)benzene,
1,2-bis(2,5-diisopropylphospholano)benzene,
1-(2,5-dimethylphospholano)-2-(diphenylphosphino)benzene,
and 1,1'-bis(2,4-diethylphosphotano)ferrocene.

The catalyst used in the invention is a catalyst containing rhodium metal and an optically active bisphosphine, as described above, as catalytic components, and is a compound represented by the following general formula (3).

$$[Rh(L)_m(Y)_n]X \quad (3)$$

(In the formula (3), L is an optically active bisphosphine represented by $R^3R^4P\text{-}Q\text{-}PR^5R^6$; Y is a nonconjugated diene compound; X is a counter anion; m is an integer 1 or 2; n is an integer 0 or 1; when m is 1, n is 0 or n is 1; when m is 2, n is 0. $R^3$, $R^4$, $R^5$, and $R^6$ independently are an aryl group optionally having a substituent group, a cycloalkyl group optionally having a substituent group or an alkyl group optionally having a substituent group; $R^3$ in combination with $R^4$ and/or $R^5$ in combination with $R^6$ may form a ring; and Q is a divalent arylene group optionally having a substituent group or a ferrocenediyl group optionally having a substituent group.)

The optically active bisphosphine denoted by L, that is $R^3R^4P\text{-}Q\text{-}PR^5R^6$, in the above formula, is as described above.

Next, the compound represented by the general formula (3) as an example of the catalyst containing rhodium metal and the optically active bisphosphine used in the invention will be described in more detail.

In the general formula (3), the non-conjugated diene compound denoted by Y may be cyclic or acyclic, and in the case where the non-conjugated diene compound is a cyclic non-conjugated diene compound, the compound may include monocyclic, polycyclic, condensed cyclic or bicyclo compounds. Furthermore, the non-conjugated diene compound may include, for example, a non-conjugated diene compound having a substituent group, that is, a substituted non-conjugated diene compound, and the substituent group is not particularly limited as long as it does not negatively affect the production method of the invention. Preferable non-conjugated diene compounds are, for example, 1,5-cyclooctadiene, bicyclo[2,2,1]hepta-2,5-diene, and 1,5-hexadiene.

In the general formula (3), the counter anion denoted by X include, for example, chloride ion, bromide ion, iodide ion, $BF_4$, $ClO_4$, $CF_3SO_3$ (hereafter abbreviated as OTf), $PF_6$, $SbF_6$, $B(3,5\text{-}(CF_3)_2C_6H_3)_4$, and $BPh_4$.

The compound represented by the general formula (3) used in the invention can be obtained, for example, by a conventionally known method as shown in the following scheme 2 under an inert gas atmosphere; or by counter-anion-exchange reaction with MX (M is a monovalent metal cation; and X is the same as described above) and subsequently by reacting a commercially available rhodium-olefin complex with an optically active bisphosphine denoted by L in an organic solvent such as methanol, ethanol, isopropanol, butanol, toluene, or tetrahydrofuran (accordingly, a compound (A) or (B) in the scheme 2 can be obtained), and optionally by further eliminating the non-conjugated diene by reacting the obtained compound with hydrogen gas (accordingly, a compound (C) in the scheme 2 can be obtained). Alternatively, the compound can be obtained by reaction of 2 equivalent rhodium-olefin complex with an optically active bisphosphine denoted by the above L in an organic solvent such as methanol, ethanol, isopropanol, butanol, toluene, or tetrahydrofuran, and by successive counter-anion-exchange reaction with MX (accordingly, a compound (B) in the scheme 2 can be obtained). The COD in the chemical formula is 1,5-cyclooctadiene.

SCHEME 2

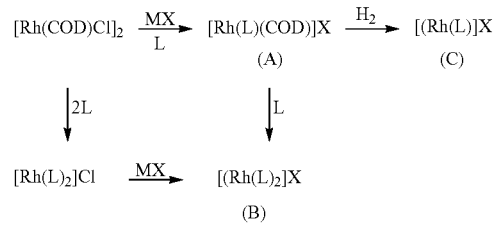

As shown in the following scheme 3, the compound represented by the general formula (3) used in the invention can be obtained also by reacting a rhodium-bisolefin complex previously subjected to counter-anion exchange reaction with an optically active bisphosphine denoted by L and optionally by further eliminating the non-conjugated diene with hydrogen gas.

SCHEME 3

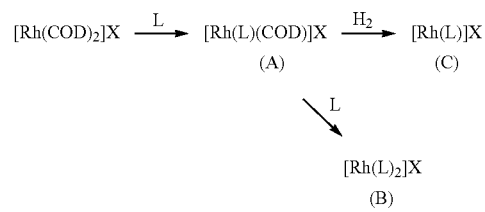

The amount of the optically active bisphosphine denoted by L to be added per mole of the center metal of the rhodium-olefin complex shown in the scheme 2 or the scheme 3 is preferably 1.0 to 2.4-fold moles, more preferably 1.05 to 2.2-fold moles since some part of the bisphosphine may be oxidized.

In the present invention, the rhodium-olefin complex used for producing the compound represented by the general formula (3) as the catalyst may be any of various complexes depending on the selected olefin ligand. However, for reasons of availability, a rhodium complex of 1,5-cyclooctadiene [Rh(COD)Cl]$_2$ and a rhodium complex of norbornadiene [Rh(NBD)Cl]$_2$ are particularly preferable.

In the counter-anion-exchange reaction, for example, silver salt (AgX) is preferably used as MX in terms of the handling easiness.

The catalytic active species in the compound represented by the general formula (3) is [Rh(L)$_m$]X. However, a precursor thereof, for example, the compound (A): [Rh(L)(COD)]X in the above-mentioned scheme, may also be used in the production method of the invention.

The compounds represented by the general formula (3) such as compounds (A), (B), and (C) in the above-mentioned scheme can be used for the production method of the invention without further purification after being prepared as a catalyst. Furthermore, in the production method of the invention, the catalyst containing rhodium metal and an optically active bisphosphine can be used immediately after the preparation thereof. Specifically, a rhodium compound and an optically active bisphosphine are reacted to prepare the catalyst, and subsequently a reactive substrate may be added.

The reaction solvent used in the production method of the invention is not particularly limited as long as it does not cause any adverse effect on the reaction, and examples may include amides such as N,N-dimethylformamide, formamide, and N,N-dimethylacetamide; halohydrocarbons such as dichloromethane, 1,2-dichloroethane, chloroform, carbon tetrachloride, and o-dichlorobenzene; aliphatic hydrocarbons such as pentane, hexane, heptane, octane, decane, and cyclohexane; aromatic hydrocarbons such as benzene, toluene, and xylene; non-nucleophilic alcohols such as tert-butanol; ethers such as diethyl ether, diisopropyl ether, tert-butyl methyl ether, dimethoxyethane, ethylene glycol diethyl ether, tetrahydrofuran, 1,4-dioxane, and 1,3-dioxolane; and sulfoxides such as dimethyl sulfoxide. These reaction solvents may be used alone or in a suitable combination of two or more thereof.

In the production method of the invention, the usage of about 1 to 10 mol % of the catalyst containing rhodium metal and an optically active bisphosphine in terms of rhodium metal, to one of the reaction substrates, is typically sufficient.

In the production method of the invention, the reaction temperature for a [2+2+2] cycloaddition reaction differs in accordance with the substrate used. However it is typically −20° C. to 100° C. and preferably in a range of 0° C. to 50° C. The reaction time naturally differs in accordance with the substrate used. However, it is typically 30 minutes to 30 hours and preferably 1 hour to 20 hours. The reaction is preferably carried out in an inert gas such as nitrogen or argon.

In addition, with respect to the phosphorus compound represented by the formula (5), a compound in which a1 and a2 are 0 can easily be produced by a conventional reaction (e.g. a method of reduction reaction by trichlorosilane) of a compound in which corresponding a1 and a2 are 1.

On completion of the reaction, post-treatment which is routinely carried out in this kind of field such as filtration, silica gel column chromatography, or the like is carried out, and purification such as crystallization, distillation, and various kinds of chromatography may be carried out alone or in combination to obtain an aimed optically active phosphorus compound.

EXAMPLES

Hereinafter, the invention will be more specifically described by referring to the examples below. However, the invention is not limited to the illustrated examples.

Example 1

Preparation of Optically Active Biaryl Phosphine (1) Preparation of diphenylphosphinoyltriyne

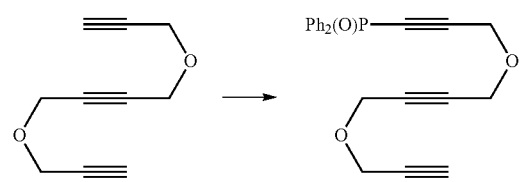

Under an argon atmosphere, chlorodiphenylphosphine (4.95 g, 22.4 mmol) was added to a 100 ml of toluene solution of 1,4-bis(propyne-2-yloxy)-2-butyne (5.45 g, 33.6 mmol), copper iodide (0.213 g, 1.12 mmol) and triethylamine (9.37 ml, 67.2 mmol) at room temperature, the mixture was stirred for 20 hours. Water was added to the reaction mixture, extraction with ethyl acetate, the organic layer was washed with saturated aqueous ammonium chloride and brine, then drying by sodium sulfate. After the solvent was evaporated, methylene chloride (80 ml) was added to the residue, 30% hydrogen peroxide (7.0 ml) was added to the solution at 0° C., the mixture was stirred for 3 hours. Water was added to the solution, extraction with methylene chloride, the organic layer was washed with brine, drying with sodium sulfate. The solvent was evaporated, subsequent purification by silica gel columun chlomatography (ethyl acetate) gave 3.95 g of triyne compound as pale yellow oil in a yield of 32%.

$^1$H-NMR (CDCl$_3$, 300 MHz): δ 7.89-7.76 (m, 4H), 7.60-7.43 (m, 6H), 4.46 (d, J=3.0 Hz, 2H), 4.32 (t, J=1.7 Hz, 2H), 4.30 (t, J=1.7 Hz, 2H), 4.24 (d, J=2.4 Hz, 2H), 2.46 (t, J=2.4 Hz, 1H); $^{31}$P-NMR (CDCl$_3$, 121 MHz): δ 8.61

(2) Preparation of bisdiphenylphosphinoylhexayne Compound

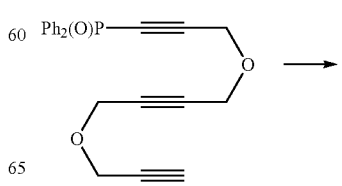

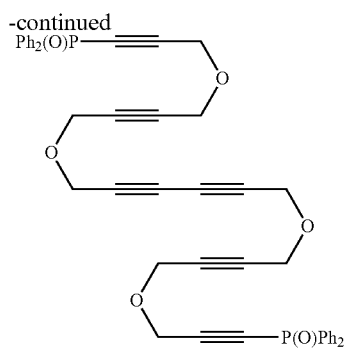

Under an argon atmosphere, a 5.0 ml of acetonitrile solution of triyne compound obtained by above example 1 (1) (0.644 g, 1.777 mmol) was added to a 5.0 ml of acetonitrile suspension of copper acetate monohydrate (1.60 g, 8.00 mmol) at room temperature, the mixture was stirred for 6.5 hours. A saturated aqueous sodium hydrogen carbonate was added to the reaction mixture, extraction with ethyl acetate, the organic layer was washed with saturated aqueous sodium hydrogen carbonate and brine, then drying with sodium sulfate. The solvent was evaporated, subsequent purification by silica gel columun chlomatography (ethyl acetate) gave 0.368 g of hexayne compound as pale yellow oil in a yield of 57%.

$^1$H-NMR (CDCl$_3$, 300 MHz): δ 7.89-7.76 (m, 8H), 7.61-7.42 (m, 12H), 4.46 (d, J=3.0 Hz, 4H), 4.32 (t, J=1.7 Hz, 4H), 4.30 (s, 4H), 4.28 (t, J=1.7 Hz, 4H); $^{13}$C-NMR (CDCl$_3$, 121 MHz): δ 133.0, 132.6 (d, J=1.9 Hz), 131.8, 131.0 (d, J=11.5 Hz), 128.8 (d, J=13.4 Hz), 101.9 (d, J=26.7 Hz), 82.8, 82.3, 81.9, 80.7, 74.8, 71.0, 57.5, 57.1, 57.0, 56.9 (d, J=2.9 Hz); $^{31}$P-NMR (CDCl$_3$, 121 MHz): δ 8.62;

(3) Preparation of Optically Active biarylphosphine Oxide

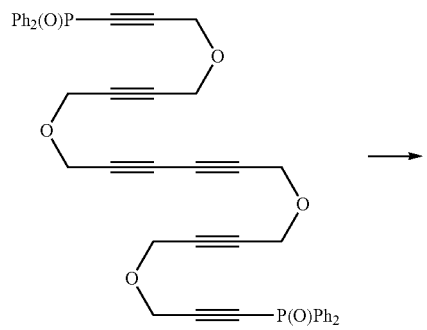

Under an argon atmosphere, a 1.0 ml of methylene chloride solution of (S)-tol-binap (3.4 mg, 0.0050 mmol) was added to a 1.0 ml of methylene chloride solution of [Rh(COD)$_2$]BF$_4$ (2.0 mg, 0.0050 mmol), and stirred for 30 minutes. Then, hydrogen gas was introduced into the schlenk tube, and the mixture was stirred for 1 hour. Successively, the reaction mixture was concentrated to dryness in vacuo, and 0.5 mL of methylene chloride was added thereto. To the mixture, a 1.5 ml of methylene chloride solution of hexayne compound obtained by above example 1 (2) (36.1 mg, 0.0500 mmol), then, the mixture was stirred at room temperature for 16 hours. Concentration of the reaction mixture and subsequent purification by thin-layer chromatography (ethyl acetate/methanol=20/1) gave 16.6 mg of the target material as a colorless solid in a yield of 46%. The optical purity of the obtained target material was 91% ee.

(4) Preparation of Optically Active biarylphosphine Oxide Having Higher Enantio Excess Rate The optically active biarylphosphine oxide obtained by example 1 (3) 28.8 mg (91% ee) was recrystallized with ethyl acetate, the optically active biarylphosphine oxide having higher enantio excess rate was given 23.9 mg (more than 99% ee). m.p. 185° C.; [α]$^{25}_D$ −5.66° (c 0.995, CHCl$_3$, >99% ee); IR (KBr): 3054, 2925, 2852, 1231, 1185 cm$^{-1}$; $^1$H NMR (CDCl$_3$, 300 MHz): δ 7.86-7.74 (m, 4H), 7.69-7.38 (m, 12H), 7.37-7.28 (m, 4H), 5.04-4.78 (m, 8H), 4.50-4.36 (m, 4H), 4.27 (d, J=12.6 Hz, 2H), 3.78 (d, J=13.4 Hz, 2H); $^{13}$C NMR (CDCl$_3$, 75 MHz): δ 142.6, 142.4, 139.0, 138.8, 137.99, 137.95, 137.90, 137.85, 135.9, 135.8, 135.1, 133.7, 132.7, 132.64, 132.56, 132.5, 132.2, 132.1, 132.0, 131.9, 131.74, 131.70, 130.8, 128.8, 128.7, 128.6, 128.4, 123.7, 122.4, 74.6, 74.5, 73.50, 73.49, 72.8, 71.5; $^{31}$P NMR (CDCl$_3$, 121 MHz): δ 28.9; HRMS (ESI) calcd for C$_{44}$H$_{36}$O$_6$P$_2$Na [M+Na ]+745.1879. found 745.1871; CHIRALPAK AD-H, hexane/IPA=80:20, 0.8 mL/min, retention times: 22.4 min (minor isomer) and 30.1 min (major isomer).

(5) Preparation of Optically Active biarylphosphine

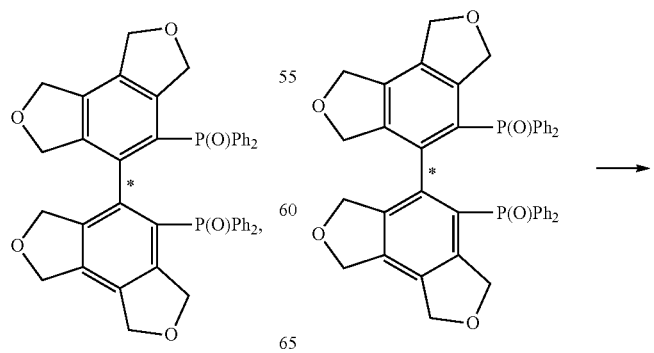

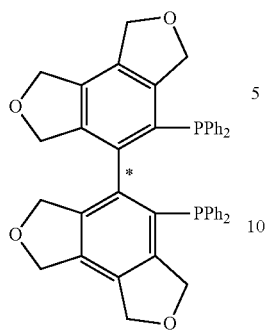

Under a nitrogen atmosphere, a mixture of trichlorosilane 670 mg (4.91 mmol), N,N-dimethylaniline 41.9 mg (0.346 mmol) and xylene 10 ml was stirred for 30 minutes at room temperature. Then, xylene (4.0 ml) solution of optically active biarylphosphine oxide obtained by above example 1 (4) 25.0 mg (0.0350 mmol) was added thereto at room temperature. The mixture was refluxed for 21 hours, then cooling down to 0° C. A 1M aqueous sodium hydroxide was added thereto, the mixture was stirred for 1 hour at 60° C., then cooling to room temperature. Water was added thereto, the mixture was extracted with ethyl acetate, and the organic layer was washed with brine, then drying with sodium sulfate. The solvent was evaporated, subsequent purification by thin-layer chlomatography (hexane/ethyl acetate=1/1) gave 21.3 mg of target compound as a colorless solid in a yield of 89%. The optical purity of the obtained target material was more than 99% ee.

m.p.: 160.2-161.5° C.; $[\alpha]^{25}_D$ +31.6° (c 0.995, CHCl$_3$, >99% ee); IR (KBr): 3051, 2940, 2845, 1434 cm$^{-1}$; $^1$H NMR (CDCl$_3$, 300 MHz): δ 7.39-7.33 (m, 6H), 7.28-7.15 (m, 14H), 5.05-4.84 (m, 8H), 4.48 (d, J=12.6 Hz, 2H), 4.28 (d, J=13.4 Hz, 2H), 4.14 (d, J=12.6 Hz, 2H), 3.82 (d, J=13.4 Hz, 2H); $^{13}$C NMR (CDCl$_3$, 75 MHz): δ 145.6, 145.54, 145.51, 139.82, 139.80, 139.5, 139.3, 139.23, 139.20, 139.18, 139.15, 136.2, 136.09, 136.06, 136.0, 135.8, 134.3, 133.93, 133.86, 133.8, 133.5, 133.4, 133.25, 133.19, 133.1, 133.0, 132.0, 131.9, 131.8, 131.6, 131.5, 129.1, 128.9, 128.84, 128.80, 128.6, 128.53, 128.50, 128.45, 128.39, 128.35, 128.30, 128.2, 73.6, 73.4, 72.6, 71.3; $^{31}$P NMR (CDCl$_3$, 121 MHz): δ 294.4; HRMS (ESI) calcd for C$_{44}$H$_{36}$O$_4$P$_2$Na [M+Na]+713.1981. found 713.1960

Examples 2 to 5

The results obtained according to the method of Example 1 (3) are shown in Table 1 below.

TABLE 1

| Example | Optically active bisphosphine | Yield (%) | Optical purity and Optical rotation |
|---|---|---|---|
| 2 | (R)-H8-BINAP | 44 | 58% ee, (+) |
| 3 | (R)-Segphos | 8 | 78% ee, (+) |
| 4 | (R)-Binap | 30 | 82% ee, (+) |
| 5 | (R)-tol-BINAP | 46 | 92% ee, (+) |

Example 6

Application to an Asymmetric Hydrogenation Reaction (1) Asymmetric Hydrogenation of Enamide with Rhodium Complex

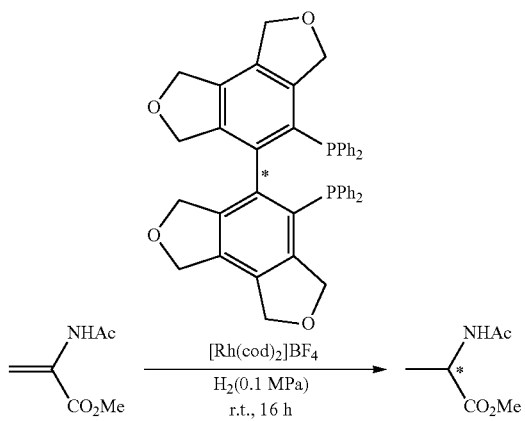

Under a nitrogen atmosphere, a solution (0.5 mL) of the optically active biarylphosphine obtained in the above Example 5 (4.5 mg, 0.0065 mmol) was added to a solution (0.5 mL) of [Rh(COD)$_2$]BF$_4$ (2.6 mg, 0.0065 mmol) in a schlenk tube, and stirred at room temperature for 15 minutes. A solution (1.5 mL) of methyl 2-acetamideacrylate (18.6 mg, 0.13 mmol) was added thereto, the mixture was stirred for 1 hour at room temperature. Then, hydrogen gas was induced to the schlenk tube, the mixture was stirred for 16 hours at room temperature. The reaction solution was evaporated, subsequent purification by thin layer chromatography (ethyl acetate) gave a compound which was directly analyzed by gas chromatography. The results are shown in Table 2, the configuration of compounds are (R).

TABLE 2

| Solvent | Conversion rate | Optical purity |
|---|---|---|
| MeOH | 100% | 73% ee |
| (CH$_2$Cl$_2$) | 100% | 96% ee |

(2) Asymmetric Hydrogenation of Enamide with Ruthenium Complex

Under a nitrogen atmosphere, a mixture of optically active biarylphosphine obtained in the above Example 5 (47.4 mg, 0.069 mmol), [RuCl$_2$(p-cymene)]$_2$ (21.0 mg, 0.034 mmol), ethanol (2.0 mL) and toluene (1.0 mL) was stirred at 50° C. for 2 hours. The resultant reaction mixture was dried, then the ruthenium complex (3.4 mg, 0.0034 mmol) obtained by the drying, methyl 2-acetamideacrylate (510 mg, 3.56 mmol) and 1.5 mL of methanol were placed in an autoclave. Then, hydrogen gas was charged to 3.0 MPa, and the reaction solution was stirred at 90° C. for 3.5 hours. The conversion rate and optical purity of the resultant product were determined by GC, they were 100% and 82% ee respectively, and the configuration was (R).

The invention claimed is:

1. An optically active compound represented by the following formula (5):

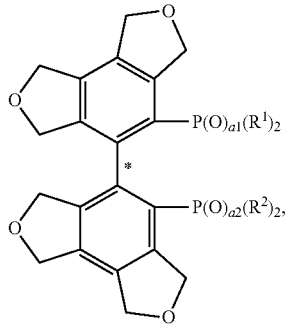

(5)

(wherein, in the formula (5), $R^1$ and $R^2$ may be the same or different are an alkyl group optionally having a substituent group selected from the group consisting of an alkoxy group and a halogen atom, a cycloalkyl group optionally having a substituent group selected from the group consisting of an alkoxy group and a halogen atom, an aryl group optionally having a substituent group selected from the group consisting of an alkyl group, an alkoxy group and a halogen atom, an alkoxy group optionally having a substituent group selected from the group consisting of a halogen atom and an aryl group or an aryloxy group optionally having a substituent group selected from the group consisting of an alkyl group, an alkoxy group and a halogen atom; a1 and a2 independently are 0 or 1; and * is axial) asymmetry.

2. A method for producing an optically active compound represented by the following formula (5), which comprises an intramolecular cycloaddition reaction of a compound represented by the following formula (2) with the use of a catalyst containing rhodium metal and an optically active bisphosphine:

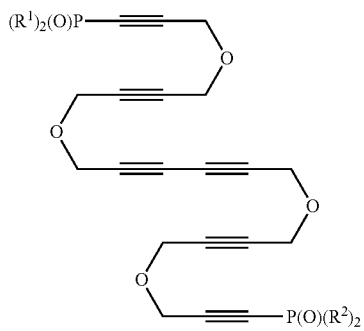

(2)

(wherein, in the formula (2), $R^1$ and $R^2$ may be the same or different are an alkyl group optionally having a substituent group selected from the group consisting of an alkoxy group and a halogen atom, a cycloalkyl group optionally having a substituent group selected from the group consisting of an alkoxy group and a halogen atom, an aryl group optionally having a substituent group selected from the group consisting of an alkyl group, an alkoxy group and a halogen atom, an alkoxy group optionally having a substituent group selected from the group consisting of a halogen atom and an aryl group or an aryloxy group optionally having a substituent group selected from the group consisting of an alkyl group, an alkoxy group and a halogen atom;

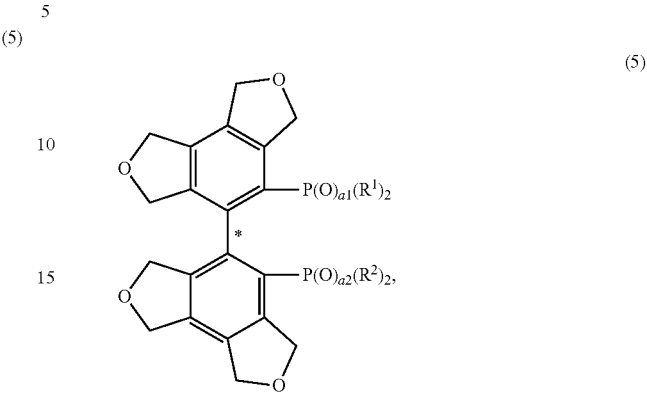

(5)

(wherein, in the formula (5), $R^1$ and $R^2$ may be the same or different and are an alkyl group optionally having a substituent group selected from the group consisting of an alkoxy group and a halogen atom, a cycloalkyl group optionally having a substituent group selected from the group consisting of an alkoxy group and a halogen atom, an aryl group optionally having a substituent group selected from the group consisting of an alkyl group, an alkoxy group and a halogen atom, an alkoxy group optionally having a substituent group selected from the group consisting of a halogen atom and an aryl group or an aryloxy group optionally having a substituent group selected from the group consisting of an alkyl group, an alkoxy group and a halogen atom; a1 and a2 independently are 0 or 1; and * is axial) asymmetry.

3. The method according to claim 2, wherein the catalyst containing rhodium metal and an optically active bisphosphine is a compound represented by the following formula (3):

$$[Rh(L)_m(Y)_n]X \qquad (3)$$

(wherein, in the formula (3), L is an optically active bisphosphine represented by the following formula (4); Y is a nonconjugated diene compound; X is a counter anion; m is an integer 1 or 2; n is an integer 0 or 1; when m is 1, n is 0 or n is 1; and when m is 2, n is 0:

$$R^3R^4P\text{-}Q\text{-}PR^5R^6 \qquad (4)$$

(wherein, in the formula (4), $R^3$, $R^4$, $R^5$, and $R^6$ independently are an aryl group optionally having a substituent group selected from the group consisting of an alkyl group, an alkoxy group and a halogen atom, a cycloalkyl group optionally having a substituent group selected from the group consisting of an alkoxy group and a halogen atom or an alkyl group optionally having a substituent group selected from the group consisting of an alkoxy group and a halogen atom; $R^3$ in combination with $R^4$ and/or $R^5$ in combination with $R^6$ may form a ring; and Q is a divalent arylene group optionally having a substituent group selected from the group consisting of an alkyl group, an alkoxy group, an alkylenedioxy group, a hydroxyl group, an amino group and a substituted amino group.

4. The method according to claim 3, wherein a nonconjugated diene compound is eliminated with the use of hydrogen gas in preparing the catalyst containing rhodium metal and an optically active bisphosphine.

5. The method according to claim 2, wherein the compound of formula (5) is a compound represented by the following formula (1),

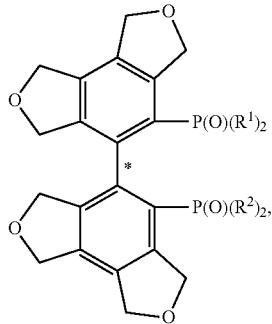

(1)

(wherein, in the formula (1), $R^1$ and $R^2$ may be the same or different and are an alkyl group optionally having a substituent group selected from the group consisting of an alkoxy group and a halogen atom, a cycloalkyl group optionally having a substituent group selected from the group consisting of an alkoxy group and a halogen atom, an aryl group optionally having a substituent group selected from the group consisting of an alkyl group, an alkoxy group and a halogen atom, an alkoxy group optionally having a substituent group selected from the group consisting of a halogen atom and an aryl group or an aryloxy group optionally having a substituent group selected from the group consisting of an alkyl group, an alkoxy group and a halogen atom; and * is axial) asymmetry.

6. A compound represented by the following formula (2):

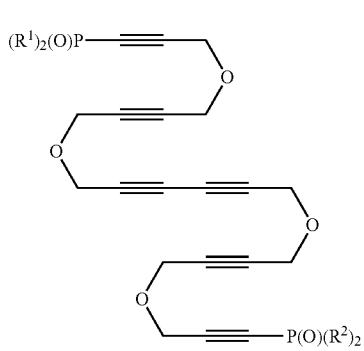

(2)

(wherein, in the formula (2), $R^1$ and $R^2$ may be the same or different are an alkyl group optionally having a substituent group selected from the group consisting of an alkoxy group and a halogen atom, a cycloalkyl group optionally having a substituent group selected from the group consisting of an alkoxy group and a halogen atom, an aryl group optionally having a substituent group selected from the group consisting of an alkyl group, an alkoxy group and a halogen atom, an alkoxy group optionally having a substituent group selected from the group consisting of a halogen atom and an aryl group or an aryloxy group optionally having a substituent group selected from the group consisting of an alkyl group, an alkoxy group and a halogen atom.

* * * * *